United States Patent [19]
Schöttes et al.

[11] Patent Number: 5,236,426
[45] Date of Patent: Aug. 17, 1993

[54] APPARATUS FOR IRRIGATING AND DRAINING WOUNDS

[76] Inventors: Philipp Schöttes, Winsheimstr. 14, 5810 Witten 5 (Rüdinghausen); Martin Scheffran, Schüruferstr. 187, 4600 Dortmund 30 (Schüren), both of Fed. Rep. of Germany

[21] Appl. No.: 692,605

[22] Filed: Apr. 29, 1991

[30] Foreign Application Priority Data

May 14, 1990 [DE] Fed. Rep. of Germany ... 9005448[U]
Dec. 27, 1990 [DE] Fed. Rep. of Germany ... 9017505[U]

[51] Int. Cl.$^5$ .............................................. A61F 5/44
[52] U.S. Cl. .................................. 604/33.4; 604/277; 604/339
[58] Field of Search .............................. 604/277-278, 604/332-345, 30, 43, 31, 133, 141, 290, 355, 357

[56] References Cited

U.S. PATENT DOCUMENTS

| | | | |
|---|---|---|---|
| 2,176,391 | 10/1939 | Chambers | 604/278 |
| 2,223,566 | 12/1940 | Koch | 604/334 |
| 4,300,560 | 11/1981 | Steer et al. | 604/335 |
| 4,553,967 | 11/1985 | Fesguson et al. | 604/334 |

Primary Examiner—David Isabella
Assistant Examiner—R. Clarke
Attorney, Agent, or Firm—Bruce L. Adams; Van C. Wilks

[57] ABSTRACT

The invention relates to an apparatus for irrigating and draining body wounds of patients, having a base plate, which can be sealingly fixed to the area surrounding a wound and which has an opening for the passage of tubes and lines and which is provided with a closed bag fixed or fixable in sealing manner to the base plate and which is provided with an opening in the fixing area. The apparatus can also be used for treating animal wounds.

30 Claims, 2 Drawing Sheets

APPARATUS FOR IRRIGATING AND DRAINING WOUNDS

BACKGROUND OF THE INVENTION

1. Field of the Invention

The invention relates to an apparatus for irrigating and draining body wounds of patients, having a base plate, which can be sealingly fixed to the area surrounding a wound and which has an opening for the passage of tubes and lines and which is provided with a closed bag fixed or fixable in sealing manner to the base plate and which is provided with an opening in the fixing area. The apparatus can also be used for treating animal wounds.

2. Description of the Prior Art

In an apparatus of the aforementioned type known from U.S. Pat. No. 4,553,967, the bag has several openings which can be individually sealingly closed by means of covers and which face the lower bag opening aligned with the base plate opening. As required, it is possible to sealingly connect to the bag at one of the openings an irrigating apparatus constituted by several components. As desired, it is also possible to sealingly connect to one of these openings a catheter holding device comprising a set of components for the purpose of draining the wound. A further opening in the bag wall positioned directly alongside the bag opening and which is aligned with the base plate opening, is used for manipulation purposes when fixing the bag and for emptying the bag into a container or for the connection of a sleeve used for emptying into a container positioned alongside the patient's bed.

This known apparatus comprises a plurality of components and devices connectable for different purposes to the bag by means of separate openings, which can be individually sealed by covers, so that the apparatus costs are high. By means of the irrigating apparatus, irrigating liquid can only be introduced from the outside into the bag, so that, if at all, only the surface of the wound area can be reached by the irrigating liquid. A wound drainage catheter whose front open end is normally inserted in the wound area during an operation is very difficult to manipulate with the device provided for wound drainage, particularly as said device must first be sealingly fitted to the bag.

Bag emptying via the large opening remains problematical due to the unavoidable unpleasant odors in the surrounding area. Unpleasant odors also occur when removing secretions from the wound area via the catheter into a container or the like. In addition, in the known apparatus, as a result of the large number of devices connectable to the bag, there is a large number of disturbing plastic parts on the bag and therefore on the patient's body.

In the apparatus known from U.S. Pat. No. 4,790,833, it is only possible to empty the bag via a tube connection inserted in the bag wall and which can be closed with a plug or stopper. Lines or tubes are not passed through the bag wall. However, the bag can be inverted over a wound catheter, which is separately fixed. A similar emptying occurs in the case of the apparatus known from German Patent 32 16 523. A different type of bag known from European Patent 286 229 is emptied by means of a valve. U.S. Pat. No. 4,449,970 and German Patent 24 42 087 merely show difficultly manipulatable bags for covering and possibly also draining wounds.

Thus, at present no possibility exists for avoiding the unpleasant odors in the surrounding area when draining off secretions (e.g. pus) and irrigating liquid.

The dirtying of the patient's bed by secretions and irrigating media associated with the irrigation and drainage of wounds constitutes a considerable burden for nursing staff and makes it frequently necessary to change the bed linen.

OBJECT OF THE INVENTION

Therefore the problem exists of improving and simplifying both for the patient and for nursing staff the irrigating and draining of wounds, particularly those located in lower-lying areas and which can only be reached by catheter, so as to completely avoid the associated unpleasant odors and the dirtying of the patient's bed. The apparatus to be used must be relatively easy and inexpensive to manufacture and permit easy handling.

SUMMARY OF THE INVENTION

On the basis of the aforementioned known apparatus, this problem is inventively solved by a wound irrigating and draining apparatus having the following basic components:

a connecting part with through ducts sealingly inserted or insertable into the wall of the bag and components connected internally and externally to said ducts for the connection of tubes, a first tube insertable by its front, open end into said wound area for supplying the irrigating liquid, a second tube insertable by its front, open end into said wound area for removing the irrigating liquid and secretions, in which said first and second tubes can be passed from said wound area through said opening in said base plate and from there through said bag and can be connected to said internal components of said connecting part, and in which to said outer components of said connecting part can be connected, at random, one or more external tubes or devices for supplying irrigating liquid and/or for removing secretions and irrigating liquid.

Said base plate leads to the apparatus being fixed to the patient's body around the wound opening, and said base plate has an opening forming a passage to the wound opening for passing through lines and tubes. This opening may also be cut to size when using the apparatus. The base plate is fixed in a sealing manner, so that neither liquid nor gases can escape from the contact region between the base plate and the patient's body.

Said bag sealingly and preferably detachably fixable to the base plate opens towards the base plate opening and therefore towards the wound area. With the exception of this opening the bag is tightly closed, because it is intended to collect secretions and irrigating liquid and to form an odor seal.

The irrigating liquid is supplied by means of a first tube passed from the outside through a sealed opening into the bag and there extends through the bag to the two aligned openings of said bag and the base plate, and from there is placed in the wound area with the front open end as the catheter.

As a flexible hose, the catheter is normally inserted in the wound area at the end of an operation. Thus, the present apparatus is so constructed from the outset that the already inserted single or two catheters can be easily connected to the apparatus for supplying irrigating liquid or for removing irrigating liquid and secretions.

Thus, according to the invention, a sealed system is formed, making it possible to supply irrigating liquid via a tube from the outside to the wound to be treated and in particular to a lower-lying wound area, as well as to collect the backflowing irrigating liquid and secretions in the bag directly on the patient's body. It is also possible to carry out the subsequently explained removal of liquids via a second tube. It is also possible to introduce a tube into the wound area so as to serve only as a drainage catheter and collect the secretions in the bag, without dirtying bed linen and without causing unpleasant odors.

It is vital that the base plate is sealed with respect to the patient's body in the same way as the bag is with respect to the base plate and the tube with respect to the bag, so as to ensure the closed nature of the system. As the connecting edge of the bag, the base plate can also be constructed in one piece with the latter.

The aforementioned basic system makes it possible to supply irrigating liquid via a first tube and collect backflowing irrigating liquid and drained-off secretions in the bag. According to the invention this system is significantly supplemented in that a second tube is inserted with its front, open end into the wound area for removing irrigating liquid and secretions.

This second tube is very important and makes it possible to pass irrigating liquid through the first tube into the wound area and to drain the irrigating liquid and secretions from the wound area and from the bag via the second tube, so that the liquids can be directly disposed of without causing unpleasant odors, dirtying the patient's bed, etc. In this case the bag only serves to seal the treatment area from the outside in order to avoid odors and prevent infection of the wound area from the environment, which also collecting the irrigating liquid or secretions, which flows out during the irrigating process alongside the drainage catheter.

The bag also has another very important function, namely securing the lines and tubes to the bag. This avoids any pulling action on the wound area. In conjunction with the fixing of the bag to the body-side fixed base plate, the fixing of the two tubes ensures that if they are inserted into the wound area as catheters, they are kept in the intended position as a result of the bag fixture. Naturally, following the introduction of the irrigating liquid, drainage, in this case the return of the irrigating liquid, together with the removal of secretions, can also take place via both tubes, namely the first and second tubes.

It is appropriate for the tubes to be sealable by valves, so as to control or check the supply of irrigating liquid and also the outflow of irrigating liquid and secretions.

Besides the two tubes, a sealable outlet should be provided on the bag, so as to permit easy emptying of the latter, without having to remove it from the patient's body.

According to the invention, it is very important that a connecting part is sealingly inserted or insertable in the bag wall and said connecting part has at least one and preferably three through ducts, said ducts having internally, namely on the inside of the bag, as well as externally components which are used for connecting tubes, in particular the first and second tubes, which are connectable to inner components of the connecting part, as well as outer tubes, which in particular serve to remove or pass on to the outside secretions and backflowing irrigating liquid. In addition, to at least one of the outer components can be fitted devices, such as, e.g., syringes for introducing or supplying irrigating liquid to the first tube. In particular, the connecting part ensures a sealing passage of the tubes or the drain in the bag wall and simultaneously the connecting part permits the fitting or connection both on the inside and the outside of different types of tubes.

The apparatus equipped according to the invention can be used in many different ways for draining and/or irrigating wounds. It is important for the apparatus to be ready for any type of use once the base plate has been fixed to the patient's body, while requiring no equipping or reequipping as in the case of the aforementioned, known apparatus.

As has already been stated, a syringe with irrigating liquid can be fitted to the outer component of the duct for irrigating a wound, the first irrigating tube being connected to its inner component. After opening the valve, which is appropriately provided on the outer component, the irrigating liquid is introduced by the syringe via the duct and the first tube into the wound area for approximately one minute. The irrigating liquid flows back out of the wound area via the second tube and, at the end of the irrigating liquid introduction, also via the first tube. The second tube is also connected to an inner component of a duct of the connecting part. The removal of the irrigating liquid and secretions from the wound area normally takes place into the bag and for this purpose corresponding openings are provided on the inner component of the first and second tubes, the opening of the inner component of the first tube for irrigation purposes being easily sealable by finger pressure for the duration of liquid introduction. For the removal of the irrigating liquid and secretions from the bag, the duct of the drain provided in the connecting part is opened, so that the bag content can be drained off via an outer tube connectable to the corresponding outer component of the particular duct, following the opening of the drain valve. If the outer tube is passed into a correspondingly covered container, there is no dirtying of the bed linen or spread of unpleasant odors into the environment.

Continous irrigation processes are also possible and on this occasion the draining of the irrigating liquid and the secretions exclusively takes place via the second tube, because irrigating liquid is supplied for a longer period via the first tube. Draining either takes place into the bag or, after covering the corresponding opening on the inner component of the associated duct of the second tube, directly through the duct to the outside into an outer tube, which is mounted or correspondingly connected to the corresponding outer component of the associated duct of the connecting part.

In the same way as the interior of the bag, the two inner tubes of the inventive apparatus can be easily cleaned by the supply and removal of a corresponding irrigating liquid quantity.

In all cases, it is easily possible to manipulate the apparatus without leading to unpleasant odors or any risks of dirtying. The manipulations at the bag required in the known apparatuses are obviated, so that in the vicinity of the wound and the bag there are no painful, unpleasant manipulations for the patient.

Unlike in the prior art, in the case of the invention there is no emptying of the bag or manual manipulation through the same relatively large opening in the container wall, which could lead to very unhygienic conditions.

The subdivision of the tubes into inner and outer tubes and their connectability to the connecting part sealingly fixed in the bag wall not only allows easy operation and handling for the draining and irrigating of wounds, but also makes it possible to use standard connections or commercially available tubes, valves, connecting plugs, etc. In addition, the functions irrigating, draining, collecting liquids in the bag, removal of the liquids from said bag, etc., can be carried out in completely separated manner to which, are allocated easily operable or handlable components, while always ensuring a completely closed system.

In order to reduce the costs for the tubes, the first and second tubes, at least along part of their path in the bag, can be combined into a twin tube with two ducts. Consequently there is only one catheter with two ducts, which is to be introduced into the wound area. The tubes are preferably flexible plastic hoses enabling the apparatus to be easily adapted to the body shape and space conditions with respect to the patient.

For the same reason, it is preferable for the bag to be made from flexible and in particular transparent plastic, which also permits very easy handling and also visual checking.

The base plate should also be made from flexible material and preferably flexible plastic. However, it can also be made from liquid or gas-tight textile material, so that it can be easily and sealingly adapted to the area around a wound.

The contact surface of the base plate is preferably provided with a self-adhesive layer or an adhesive film and a cover film for protecting the self-adhesive layer or adhesive film, in order to significantly facilitate the application and sealing fixing of the base plate to the patient's body. The manufacture of the base plate from plastic, with or without an adhesive film, allows an individual adaptation to the size of the wound area and the position on the body, because both the contour shape of the base plate and also its opening can easily be adapted or cut to size by means of scissors or some other suitable cutting tool. This leads to a very flexible irrigating and drainage system easily adaptable to individual needs.

Preferably the base plate is provided with a connecting device for a detachable, sealing fixing of the bag in the vicinity of the two openings. This detachable fixing makes it possible to remove and refit the bag with respect to the base plate should this prove necessary, without it being necessary to detach the base plate from the patient's body. This is important for action in the wound area, as well as for replacing the bag and for fitting or replacing the tubular catheter or the like.

The aforementioned connecting device appropriately comprises a locking cover on the base plate opening and a locking ring surrounding the bag opening. This preferably plastic connecting device permits easy, rapid detachment of the bag from the base plate and also an easy, rapid and sealing fitting of the bag to the base plate.

In order to permit easy access to the wound area without removing the bag, according to a further development of the invention, the bag has a second opening facing the first opening on the bag side and which can be sealingly covered by means of a removable, transparent cover, preferably made from plastic. Once again the connecting device is appropriately provided with a locking ring and a locking cover. Through the opening closable by means of the cover, e.g., the end portion of the first and/or second tube can, if necessary, be removed from the wound area and optionally a new one can be introduced without it being necessary to remove the apparatus, i.e., the base plate together with the bag from the patient's body. Other manipulations are also possible through the sufficiently large opening.

A very decisive advantage of the invention is, as is shown by the subsequently described embodiments, that the apparatus for irrigating and draining wounds can be easily manufactured from already commercially available components and in part only an adaptation is necessary. This also makes it possible to use connections such as are available in hospitals and clinics, e.g., for disposing of the irrigating liquid and secretions.

Independently of the particular embodiments in which the invention is realized, it provides new possibilities for draining and irrigating abscess cavities, etc., whose treatment with the heretofore known means was extremely difficult and unpleasant both for the patient and the nursing staff. Other indications are the draining and irrigating of hematoma cavities, leaking anastomoses in the field of abdominal surgery, necrotic cavities in pancreatic inflammations, oncolysis cavities or duodenal stump dehiscences.

A very important additional part of the invention is that the first and second tubes, or the corresponding inner components of the connecting part, have openings, which can be sealed by finger pressure from the outside on the bag. As described hereinbefore in connection with the possibilities for different irrigation processes, said openings make it possible to empty the tubes into the interior of the bag. On introducing the irrigating liquid the corresponding opening on the tube or the inner component can easily be closed by finger pressure for the duration of the introduction process.

BRIEF DESCRIPTION OF THE DRAWINGS

Embodiments of the invention are described in greater detail hereinafter relative to the drawings, wherein show.

DETAILED DESCRIPTION OF THE INVENTION

Figure 1:
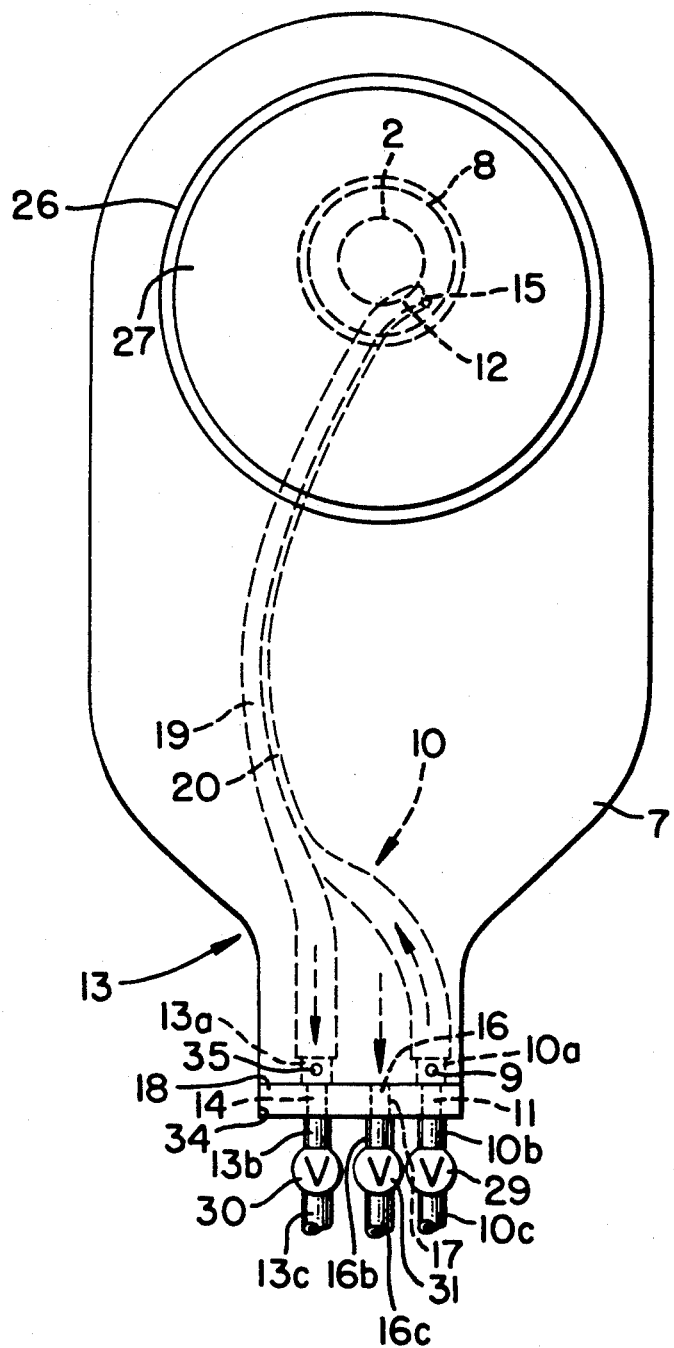
FIG. 1 a plan view of an apparatus for irrigating and draining wounds.
Figure 2:
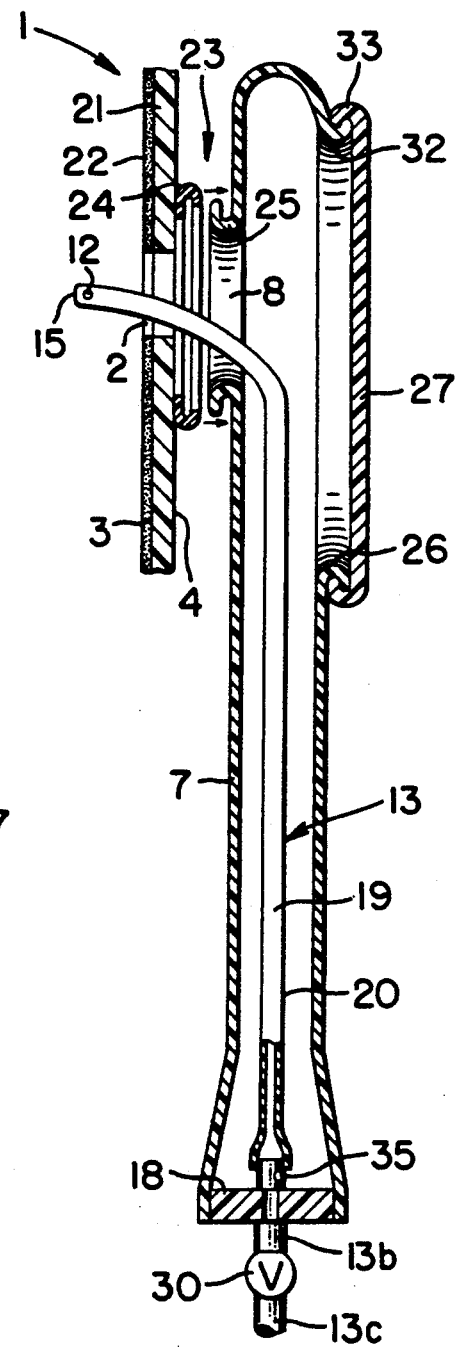
FIG. 2 a side view of the apparatus of FIG. 1 in sectional form.

The apparatus shown in FIGS. 1 and 2 has a base plate or base member 1 made from flexible material, e.g., plastic with an opening 2 and whose underside 3 can be fixed in a surrounding area 5 (cf. FIG. 3) of an only diagrammatically indicated wound 6. The wound remains accessible through the opening 2. A flexible, transparent plastic bag or flexible chamber 7 having an opening 8, which after fixing is aligned with the opening 2, is fixed either firmly or in a manner to be described hereinafter in gas and liquidtight manner to the top surface 4 of the base plate 1.

A first inner tube 10, which is in the form of a flexible and optionally transparent plastic hose, extends through the bag or chamber 7 and its opening 8 and can be inserted with its front open end 12 as a catheter into the wound 6 and appropriately in conventional manner at the end of an operation.

A second inner tube 13 can also be passed through the bag 7 and its front open end 15 can also be inserted as a catheter into the vicinity of the wound 6. The first tube 10 can be used for supplying an irrigating liquid to the wound area, while the second tube 13 is responsible for the passive removal of the irrigating liquid and the wound secretions. An outlet or drain 16 is additionally provided for removing the irrigating liquid and/or secretions from the bag 7.

The first and second inner tubes 10, 13 and the outlet 16 are connected to a common connecting part or member 18 (or shown relative to the outlet 16). which is inserted and sealingly fixed in an opening 34 at the lateral end of the bag 7. It is also made from plastic and has three through ducts 11, 14, 17 and by means of the inner and outer components 10a, 13a or 10b, 13b, 16b permits the use and connection of different types of tubes, which can be mounted in simple manner on the components 10a, 10b, 13a, 13b, 16b, which are, e.g., constructed as connecting plugs. Thus, in the interior of the bag 7 the two inner tubes 10, 13 are mounted on the two inner components 10a and 13a. The first and second tubes 10 and 13 are combined in the represented embodiment to form a twin tube with two ducts 19 and 20, so that it is only necessary to manipulate a single tube in the wound area, e.g., as a catheter.

Appropriately commercially available valves 29, 30, 31 can be connected outside of the bag or chamber 7 to the outer components 10b, 16b, 13b of the connecting part 18 and the valves can be individually opened and shut. On the other side the external valves 29, 30, 31 are connected with corresponding outer, flexible and transparent or translucent plastic hoses 10c, 13c and 16c.

The base plate 1 preferably comprises a supporting layer of flexible plastic 21 with an adhesive foil or film 22 on the underside and with a connecting device 23 surrounding the opening 2 for the disconnectable connection of the bag 7. The connecting device 23 comprises a plate-side locking cover 24 and a corresponding bag-side locking ring 25, both of these parts once again being made from a flexible plastic and when locked into one another ensure a gas and liquid-tight connection.

The inner components 10a, 13a constructed as connecting plugs in each case have discharge openings 9, 35, which are arranged in such a way that they can be closed by the pressure of the fingertip by pressing the bag wall above the same onto the particular opening 9 or 35. The discharge openings 9, 35 coact with the flexible wall of the bag 7 to define internal valves located inside of the bag.

In the position facing the openings 2, 8, a cover 27 is provided for closing an opening 26 in the wall of the bag 7. The opening is made sufficiently large for a hand to pass through it, if manipulations are necessary on the inner tubes 10, 13 etc., in the wound area. Once again, an easily detachable locking connection is used for opening and closing purposes, namely a bag-side locking ring 32 on which the cover 27 can be sealingly mounted by means of a locking rim 33.

A ventilation window 28 is provided in the cover 27 for the case that a hermetic seal of the bag 7 and therefore the wound area is not appropriate, or to occasionally vent the bag 7.

If it is unnecessary to occasionally detach the bag 7 from the base plate 1 and optionally replace it by a new bag 7, the latter can be fixed from the outset in permanent manner to the base plate 1, so that a one-piece apparatus is obtained from the start.

Figure 3:
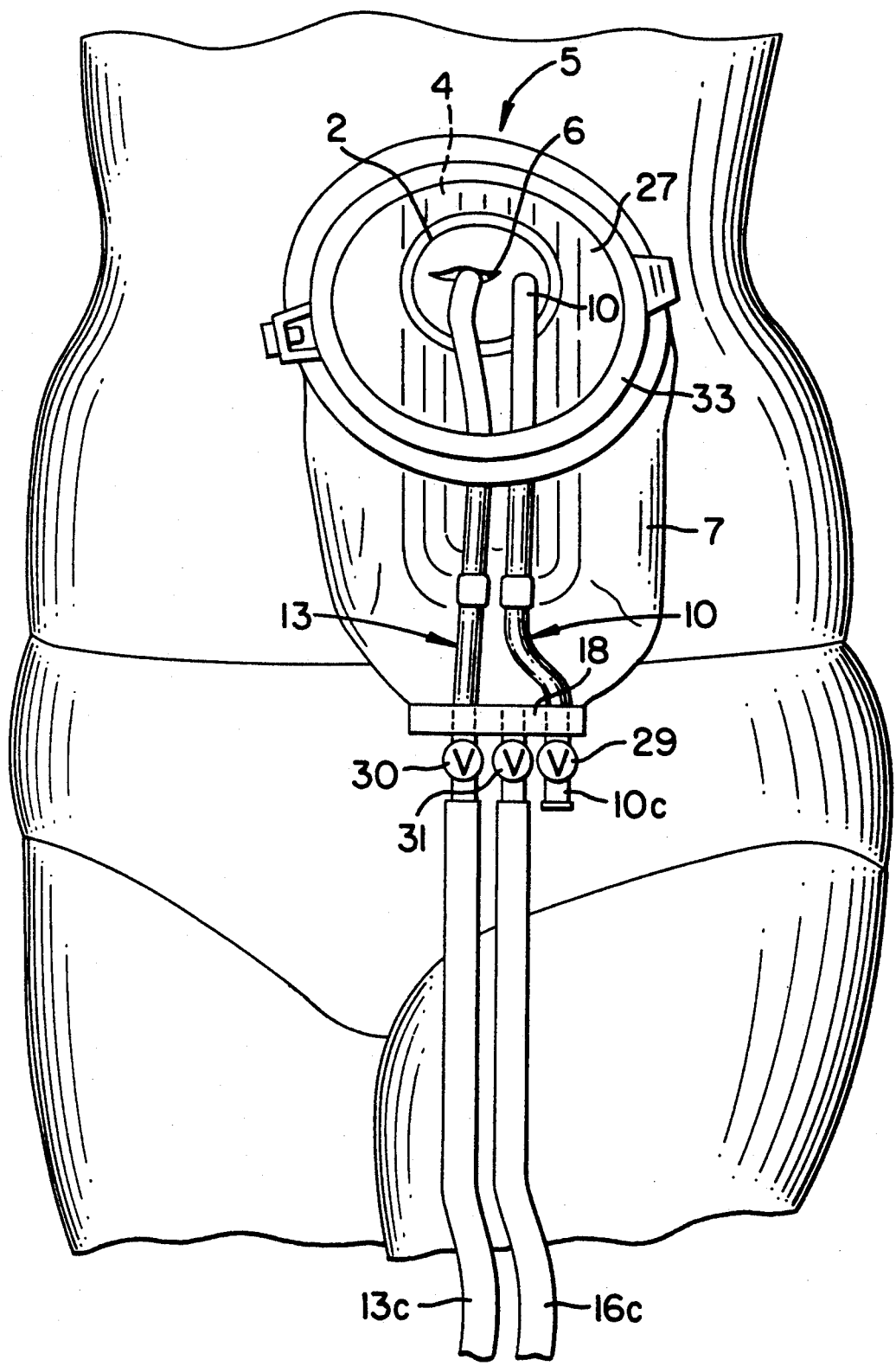
FIG. 3 a view of a wound irrigating and draining apparatus fitted to the patient in the vicinity of a wound, roughly in the manner of the preferred embodiment of FIGS. 1 and 2.

FIG. 3 demonstrates how an apparatus, e.g., in the construction according to FIGS. 1 and 2, can be fitted to the area surrounding a patient's wound. The front or leading ends 12, 15 of the here separately constructed first and second inner tubes 10,13 are introduced as catheters into the wound area and are consequently not visible. The transparent cover 27 allows a visual check. The apparatus makes it possible to irrigate and drain the wound without suffering from the heretofore unavoidable disadvantages described in the first part of the description.

In the closed system formed by the base plate 1 with the bag 7 and the two inner tubes 10, 13 for irrigating the wound area, the irrigating liquid is supplied to the wound area via the first inner tube 10. For this purpose, to the inlet of the external valve 29 is fitted a syringe with irrigating liquid, the valve 29 is opened and the opening 9 of the inner valve in the inner component 10a is closed by finger pressure. The irrigating liquid supplied to the wound area can flow away together with the wound secretions via the second, inner tube 13, namely into the bag 7 via the opening 35 in the inner component 13a. At the end of the supply of the irrigating agent, the return flow thereof can also take place via the first inner tube 10 and the opening 9 in the inner component 10a of the connecting part 18. The external valves 30, 31 are always closed during this process, whereas the external valve 29 is closed at the end of the introduction of the irrigating liquid.

The external valve 31 of the outlet 16 is opened for the removal of the liquids which have collected in the bag 7, so that when the connecting part or member 18 of the bag 7 assumes a corresponding lower position, the liquid can drain out through the duct 17, the outer component 16b, the valve 31 and the connected outer tube 16c.

When the opening 35 of the inner valve is closed by finger pressure, i.e., pressing the respecting wall of the bag 7 onto the opening 35, and when the external valve 30 is opened the liquid from the bag 7 can drain out through the duct 14.

Variations concerning the use of the apparatus for wound drainage only and also when irrigating a wound have been described hereinbefore. There is never any problem with unpleasant odors or dirtying of the bed linen as a result of the uncontrolled or open-outflowing irrigating liquid or secretions.

In a further simplified embodiment of the invention, there is no outlet or drain 16 and also no through duct 17. This is an important, but not shown embodiment of the invention because it can be easily taken from FIG. 1. Removal of irrigating liquid and/or secretions from the bag 7 is made with this embodiment via the discharge opening 35 of the internal valve in the inner component 13a, duct 14, the outer component 13b, the then opened external valve 30 and the plastic hose 13c. Without the extra outlet 16 and the other parts in the middle of the connecting part 18, advantages are obtained for the production of the connecting part 18 and for the handling of the apparatus which is now easier and more safe.

When changing the apparatus shown in FIG. 1 to the aforesaid simplified embodiment, the following parts would be removed: outlet 16, outer component 16b, plastic hose 16c, duct 17 and valve 31. Further the middle arrow above the connecting part as well as the through way shown in dotted lines in the connecting part 18 as well as the plastic hose 16c would be cancelled. In FIG. 3, plastic hose 16c, valve 31 and the through way in connecting part 18 would be removed.

An apparatus according to the invention can be assembled from commercially available components for medical equipment. Plenty of products are commercially available for an adherable base plate and a bag connectable to the latter by a locking connection. They have to be correspondingly adapted to the invention and in particular a corresponding connecting piece 18 must be sealingly inserted and provided with the necessary inner and outer components. Flexible rubber tubes, connections, valves, etc., are also commercially available. Therefore the equipment according to the invention can be very inexpensively manufactured without any significant development costs being involved.

We claim:

1. A kit comprised of component parts capable of being assembled for irrigating and draining wounds on a patient's body, comprising: a base plate sealingly fixable to the area surrounding a patient's wound and having an opening for the passage of tubes, a bag fixable in a sealing manner to said base plate and having a first opening communicating with the base plate opening and having a second opening, said base plate and said bag being made of flexible material, a connecting part inserted and fixed in a sealing manner in the second opening of said bag, components connected internally and externally to ducts in said connecting part for the connection of inner and outer tubes, a first inner tube having a front open end insertable as a catheter in the wound area primarily for supplying irrigating liquid, a second inner tube having a front open end insertable as a catheter in the wound area for removing irrigating liquid and secretions from the wound area and for introducing the irrigating liquid and secretions through a discharge opening into the bag, said first and said second inner tubes being made of flexible material and being fixable through the connecting part to said bag, said first and second inner tubes being dimensioned and configured to extend from said opening in said base plate through said bag for connecting to corresponding ones of the said internal components of said connecting parts, one first outer tube connectable to a first one of said external components of said connecting part for supplying irrigating liquid through said first inner tube into the wound, one second outer tube connectable to a second one of said external components of said connecting part for removing secretions and irrigating liquid from said bag, and valves communicating with said ducts of said connecting part for controlling the input of the irrigating liquid into and the discharge of the secretions and irrigating liquid from said bag.

2. A kit according to claim 1; further including one third outer tube connectable to a third one of said external components, and the second inner tube being connectable to one of said internal components for removing secretions and irrigating liquid from the wound area directly into said third outer tube, the discharge opening related to the second inner tube inside the bag optionally being closable.

3. A kit according to claim 1 or 2; wherein said first inner tube has a closable discharge opening located within the bag and effective when closed to permit the supply of irrigating liquid through said first inner tube and effective when open to permit the discharge of secretions and irrigating liquid from the wound area through said first inner tube into the bag.

4. A kit according to claim 1; wherein said valves are connected to said external components of said connecting part.

5. A kit according to claim 4; wherein valves are connected between said external components of said connecting part and said outer tubes.

6. A kit according to claim 1; wherein said first and second inner tubes, at least along a part of the path in said bag, are combined to form a twin tube with two ducts.

7. A kit according to claim 1; wherein said first and inner second tubes are formed from flexible plastic hoses.

8. A kit according to claim 1, wherein said bag is made from highly flexible transparent plastic material.

9. A kit according to claim 1; wherein said base plate is made from a highly flexible plastic material.

10. A kit according to claim 1; wherein said base plate has a connecting device comprised of a locking cover on said base plate, and an open locking ring, which surrounds said first opening of said bag.

11. A kit according to claim 1; wherein said bag has a third opening which is sealingly closable by means of a removable, flexible cover and is located on a side of said bag which faces the side of the first opening of said bag.

12. A kit according to claim 1; wherein said bag is constructed flat and tapers towards said connecting part, which is fixed to a lateral end of said bag positioned at the lower bag edge when the apparatus is in use.

13. A kit according to claim 1; wherein said first and second inner tubes each communicate with the interior of said bag through a discharge opening, the discharge openings being disposed so as to be closed by finger pressure from the outside on said bag.

14. A kit comprised of component parts capable of being assembled into an apparatus for irrigating and draining a patient's wound, comprising: a flexible base member having an opening therein and being attachable to the body of a patient during use of the apparatus to enable access to the patient's wound area through the base member opening; means defining a flexible chamber connected to the base member during use of the apparatus with the interior of the flexible chamber communicating with the base member opening; a first flexible tube adapted to be placed inside the flexible chamber during use of the apparatus and having a leading end dimensioned to project out of the flexible chamber through the base member opening for insertion as a catheter in the wound area and having a trailing end; a second flexible tube adapted to be placed inside the flexible chamber during use of the apparatus and having a leading end dimensioned to project out of the flexible chamber through the base member opening for insertion as a catheter in the wound area and having a trailing end; and valving means for communicating with the trailing ends of the first and second tubes during use of the apparatus and operable in a first mode to communicate the trailing ends of one or both of the first and second tubes with the interior of the flexible chamber to enable material from the wound area to drain into and collect in the flexible chamber and operable in a second mode to communicate the trailing end of the first tube with a source of irrigating liquid and to communicate the trailing end of the second tube with either the interior or the exterior of the flexible chamber to effect irrigation of the wound area with the irrigating liquid and operable in a third mode to communicate the trailing ends of one or both of the first and second tubes with the exterior of the flexible chamber to enable removal of material collected in the flexible chamber.

15. A kit according to claim 14; wherein the valving means includes first valve means for selectively communicating the trailing end of the first tube with the interior of the flexible chamber and with the exterior of the flexible chamber.

16. A kit according to claim 15; wherein the first valve means comprises a first internal valve disposed within the flexible chamber for selectively communicating the first tube trailing end with the interior of the flexible chamber, and a first external valve disposed outside of the flexible chamber for selectively communicating the first tube trailing end with the exterior of the flexible chamber.

17. A kit according to claim 15 or 16; wherein the valving means includes second valve means for selectively communicating the trailing end of the second tube with the interior of the flexible chamber and with the exterior of the flexible chamber.

18. A kit according to claim 17; wherein the second valve means comprises a second internal valve disposed within the flexible chamber for selectively communicating the second tube trailing end with the interior of the flexible chamber, and a second external valve disposed outside of the flexible chamber for selectively communicating the second tube trailing end with the exterior of the flexible chamber.

19. A kit according to claim 18; wherein the first and second internal valves comprise means defining discharge openings which communicate the respective tube trailing ends with the interior of the flexible chamber, and wall portions of the flexible chamber which can be flexed inwardly by finger pressure to close the respective discharge openings to thereby close the first and second internal valves.

20. A kit according to claim 18; including a connecting member sealingly connected to an opening in the flexible chamber, the connecting member having plural ducts extending therethrough, the first and second internal valves being connected to respective ducts inside of the flexible chamber and the first and second external valves being connected to said respective ducts outside of the flexible chamber.

21. A kit according to claim 20; wherein the valving means includes a third external valve connected to another one of the ducts outside of the flexible chamber.

22. A kit according to claim 14; wherein the valving means includes one valve means for selectively communicating the trailing end of the second tube with the interior of the flexible chamber and with the exterior of the flexible chamber.

23. A kit according to claim 22; wherein the one valve means comprises an internal valve disposed within the flexible chamber for selectively communicating the second tube trailing end with the interior of the flexible chamber, and an external valve disposed outside of the flexible chamber for selectively communicating the second tube trailing end with the exterior of the flexible chamber.

24. A kit according to claim 23; wherein the valving means includes another valve means for selectively communicating the trailing end of the first tube with the exterior of the flexible chamber.

25. A kit according to claim 24; wherein the another valve means comprises another external valve disposed outside of the flexible chamber.

26. A kit according to claim 25; wherein the valving means includes a further external valve disposed outside of the flexible chamber and communicating with the interior of the flexible chamber for selectively communicating the interior of the flexible chamber with the exterior thereof.

27. A kit according to claim 14; including means for detachably connecting the flexible chamber to the base member.

28. A kit according to claim 14; wherein the first and second tubes are combined, at least along a part of their path in the flexible chamber, to form a twin tube with two ducts.

29. A kit according to claim 14; including means defining an opening in a wall of the flexible chamber, and a cover detachably closing the opening.

30. A kit according to claim 29; wherein the opening in the flexible chamber is located opposite the opening in the base member and has sufficient size to enable a person's fingers to fit therethrough.

* * * * *